United States Patent [19]

Durand et al.

[11] Patent Number: 4,808,761

[45] Date of Patent: Feb. 28, 1989

[54] DEMETHANOLIZATION OF AQUEOUS $CH_3OH/HCL$ SOLUTIONS

[75] Inventors: Bernard Durand, Claix; Jean-Jacques Masini, Chaponost, both of France

[73] Assignee: Atochem, Puteaux, France

[21] Appl. No.: 914,077

[22] Filed: Oct. 1, 1986

[30] Foreign Application Priority Data

Oct. 1, 1985 [FR] France ................. 85 14552

[51] Int. Cl.$^4$ .............................................. C07C 17/16
[52] U.S. Cl. .................................................... 570/258
[58] Field of Search ........................................ 570/258

[56] References Cited

U.S. PATENT DOCUMENTS

| | | | |
|---|---|---|---|
| 2,153,170 | 4/1939 | Buc et al. | 570/258 |
| 3,432,561 | 3/1969 | Dadekian et al. | |
| 3,527,820 | 9/1970 | Mercier | 570/258 |
| 3,981,938 | 9/1976 | Steele et al. | 570/258 |
| 3,983,180 | 9/1976 | Habata et al. | 570/258 |

FOREIGN PATENT DOCUMENTS

| | | | |
|---|---|---|---|
| 2270224 | 12/1975 | France | 570/258 |
| 144328 | 8/1983 | Japan | 570/258 |

*Primary Examiner*—Howard T. Mars
*Attorney, Agent, or Firm*—Burns, Doane, Swecker & Mathis

[57] ABSTRACT

Residual aqueous phases, emanating from the synthesis of methyl chloride by reacting methanol with hydrochloric acid, are conveniently demethanolized by maintaining same in liquid phase and in the absence of catalyst, at a temperature of from 50° to 150° C. and under a pressure of less than about 8 bars. The methanol recovered is in the form of a crude methyl chloride which is advantageously recycled to the $CH_3OH/HCl$ reaction zone.

7 Claims, 2 Drawing Sheets

DEMETHANOLIZATION OF AQUEOUS CH₃OH/HCL SOLUTIONS

BACKGROUND OF THE INVENTION

1. Field of the Invention

The present invention relates to the elimination of unreacted methanol from aqueous residual solutions emanating from the synthesis of methyl chloride, and, more especially, to such elimination where the methanol is directly recovered in the form of methyl chloride.

2. Description of the Prior Art

It is known to this art that methyl chloride is produced industrially by reacting methanol with hydrochloric acid, in the liquid or gaseous phase, in the presence of a catalyst. In both cases, the reaction products are obtained in the gaseous form. They essentially consist of methyl chloride, water, hydrochloric acid and unreacted methanol.

The reaction products exiting the reactor are cooled to separate the methyl chloride and to recover an aqueous phase containing the excess hydrochloric acid and the unreacted methanol. The gaseous methyl chloride phase is washed with water, or with an aqueous hydrochloric acid solution having suitable HCl titer, in order to almost completely strip it of the HCl and methanol that may still be retained therein. This wash water may optionally be added to the aqueous phase for subsequent treatment.

In the synthesis of methyl chloride, the aqueous phase which contains more than 15% by weight, and typically in excess of 20% hydrochloric acid, is usually discarded, resulting not only in a loss of methanol in amounts of up to 100 g/l, and most typically from 15 to 60 g/l, but also in pollution, if the effluents are not treated prior to discharge.

SUMMARY OF THE INVENTION

Accordingly, a major object of the present invention is the provision of an improved process for the recovery of HCl and methanol values from aqueous phases emanating from the production of methyl chloride.

Briefly, this invention features transferring such residual aqueous solution, as is, into a reactor, wherein it is heated, in the absence of a catalyst, to a temperature of from 50° to 150° C., and preferably from 70° to 100° C., under a pressure of less than 8 bars, and preferably less than 5 bars. The reaction time depends essentially upon the temperature of the reaction and the initial concentration of the aqueous phase in methanol and hydrochloric acid. This treatment, carried out in the liquid phase, enables direct recovery of the methanol values in the form of crude methyl chloride, as overheads, from the top of the reactor, which is then recycled into the principal methyl chloride production unit. From the base of the reactor, a demethanolized hydrochloric acid solution is recovered, which may be used as such.

DETAILED DESCRIPTION OF THE PREFERRED EMBODIMENTS OF THE INVENTION

Figure 1:
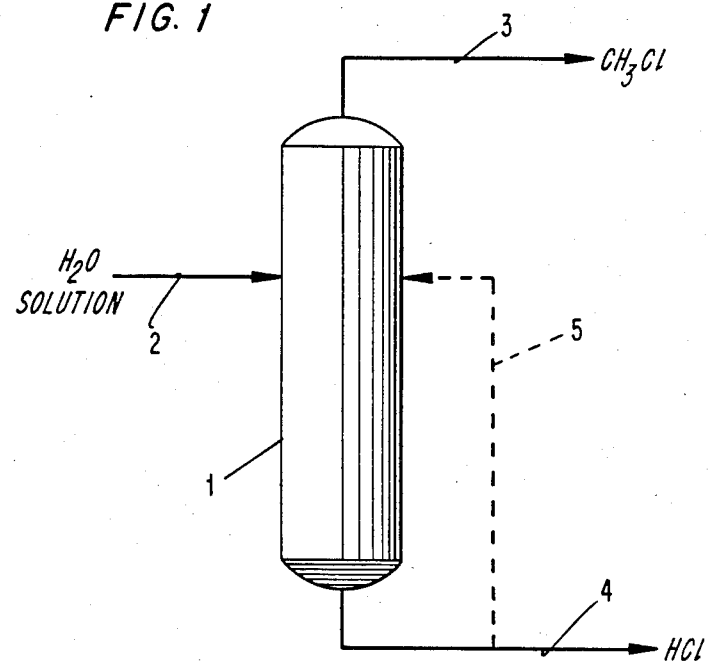
FIG. 1 is a schematic diagram of suitable process/apparatus according to the invention.

More particularly according to the present invention, in the embodiment shown in FIG. 1, the residual aqueous solution to be treated, is introduced, via the optionally preheated inlet line 2, into the reactor 1, which either may or may not be equipped with means for agitation. The crude methyl chloride is recovered as overhead through the line 3 and is recycled into the principal production unit (not shown), and through the outlet line 4 the hydrochloric acid solution is recovered. If an agitated reactor is used, any means for agitation may be employed, in particular for recirculation into the reactor of the liquid to be treated via the line 5.

Figure 2:
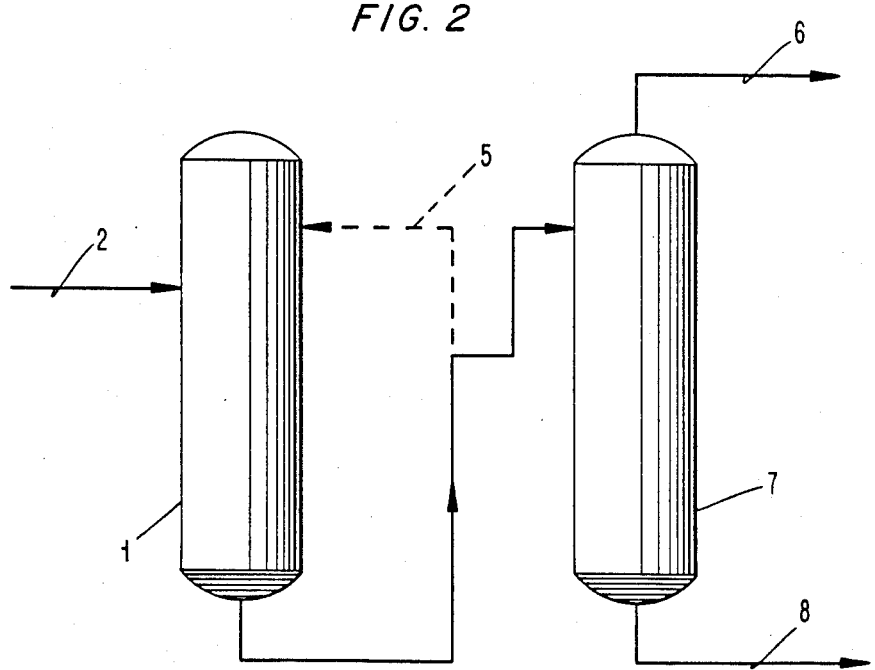
FIG. 2 is also a schematic diagram of another suitable process/apparatus according to the invention.

In order to improve the amount of methanol converted into methyl chloride, it may be advantageous to use several reactors in series, as shown, for example, in FIG. 2, wherein the crude methyl chloride is recovered via outlet line 6 from the reactor 7, with the residual hydrochloric acid solution being recovered through line 8.

Figure 3:
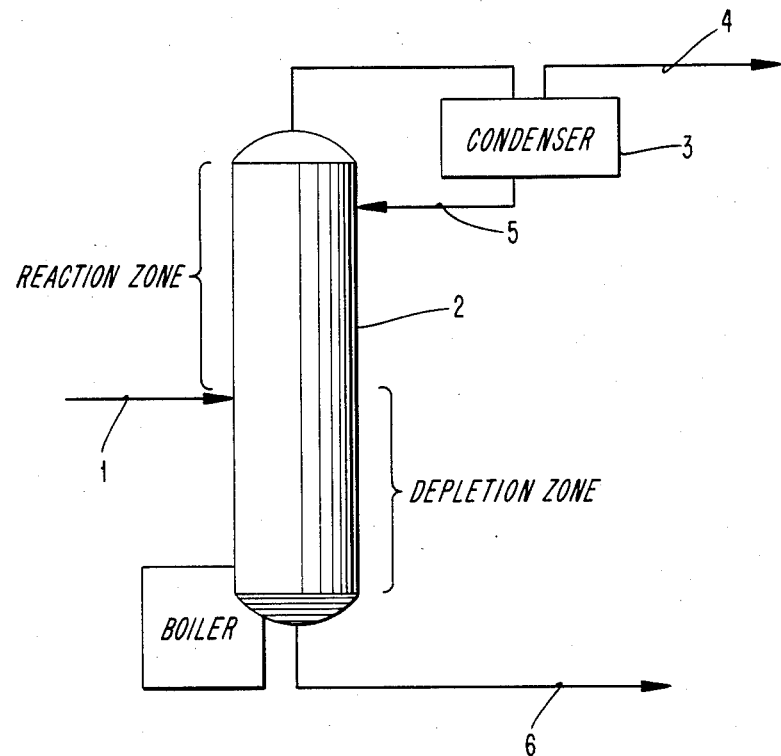
FIG. 3 is a schematic diagram of alternate process/apparatus according to the invention, including a distillation column.

In another preferred embodiment of the invention, the conventional reactor is replaced by a distillation column, in which a distillation reaction between the methanol and the hydrochloric acid is carried out. As shown in FIG. 3, the residual aqueous solution to be treated is introduced into a distillation column 2 by means of inlet line 1, the products of distillation being recovered at the top of the column, in a condenser 3, from which the crude methyl chloride formed is extracted through the line 4, with the liquid phase being returned to the distillation zone by means of the line 5. The purified hydrochloric acid solution is recovered from the base of the column, via line 6. The column is preferably charged at the level of the separation of the depletion zone and the reaction zone. The depletion zone is determined in a manner such that the desired CH₃OH/residual acid separation is assured. The reaction zone is determined as to assure a CH₃OH concentration and a retention time of the liquid phase such that the consumption of methanol by reaction with the HCl is as complete as possible. The definition of these zones depends in particular upon the dimensions of the column, operating parameters such as the pressure and the rate of reflux, and the characteristics of the contactors, e.g., of the plates and packing.

Consistent herewith, it is thus possible to usefully recover the major amount of unreacted methanol, in the form of methyl chloride, from a methyl chloride production unit, while at the same time employing residual hydrochloric acid more or less as a pollution control means.

In order to further illustrate the present invention and the advantages thereof, the following specific examples are given, it being understood that same are intended only as illustrative and in nowise limitative.

EXAMPLE 1

Into an unagitated reactor, a residual aqueous solution from the synthesis of methyl chloride was discontinuously introduced and was permitted to stand for 7 hr, 30 min, under atmospheric pressure and the temperature conditions reported in the Table below. The initial HCl and CH₃OH concentrations, and the CH₃OH concentration after said retention time, are also reported in the Table.

TABLE

| Experiments | 1 | 2 | 3 | 4 | 5 |
|---|---|---|---|---|---|
| HCl concentrations, in weight % | 30 | 25 | 32 | 25 | 29 |
| Initial CH$_3$OH concentration, in g/l | 18 | 29 | 25 | 21.5 | 21 |
| Reactor temperature, °C. | 60 | 75 | 75 | 80 | 80 |
| CH$_3$OH concentration, after 7 hr, 30 min, in g/l | 10.5 | 13.5 | 3 | 4 | 2 |

An increase in the retention time further improved the demethanolization of the residual solutions.

EXAMPLE 2

The residual solution was continuously introduced into an unagitated reactor at a rate such that the residual solution remained therein for 7 hr at 95° C., under a pressure of 4 bars. The solution initially contained 30% by weight of HCl and 30 g/l of methanol. The hydrochloric acid solution ultimately recovered contained 500 ppm methanol. The methyl chloride formed was recycled to the principal methyl chloride production unit.

EXAMPLE 3

In a series of two reactors, the first having a useful volume of 25 cm$^3$ and provided with agitation by recirculation, and the second being unagitated and having a useful volume of 18 cm$^3$, a residual solution containing 31.5% by weight of HCl and 15.45 g/l methanol was introduced at a rate of 1.8 m$^3$/hr. The temperature was 75° C. in the first reactor and 66° C. in the second, and the pressure was 1.34 bar absolute in both. The hydrochloric acid solution ultimately recovered contained 1.7 g/l methanol. The methyl chloride formed was recycled to the principal methyl chloride production unit.

EXAMPLE 4

At the base of its reaction zone, a residual solution containing 19.3% by weight of HCl and 20 g/l methanol was introduced, at a rate of 2.2 m$^3$/hr, into a glass lined distillation column having a diameter of 500 mm, a height of 8 m for the depletion zone and 4 m for the reaction zone, and fitted with a condenser at the top thereof.

At the base of the depletion zone, a hydrochloric acid solution containing 1 g/l methanol was recovered. The methyl chloride recovered at the outlet of the condenser was recycled to the principal methyl chloride production unit.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

We claim:

1. A process for the preparation of methyl chloride, comprising (i) catalytically reacting methanol with hydrochloric acid, in liquid or gaseous phase,
    (ii) cooling the reaction mixture and separating methyl chloride and an aqueous CH$_3$OH/HCl solution therefrom, and
    (iii) maintaining said aqueous solution in the liquid phase, in the absence of catalyst, at a temperature of from 50° to 150° C. under a pressure of less than about 8 bars and for a time sufficient to effect demethanolization, whereby a crude methyl chloride is recovered therefrom.

2. A process for the demethanolization of an aqueous solution comprising methanol and hydrochloric acid values, comprising the steps of maintaining such solution, in the liquid phase and in the absence of catalyst, at a temperature of from 50° to 150° C., under a pressure of less than about 8 bars and for a time sufficient to effect demethanolization, and recovering said methanol as crude methyl chloride;
    wherein said aqueous solution comprises a residual aqueous phase resulting from the reaction of methanol with hydrochloric acid in a principal methyl chloride production unit to produce methyl chloride, wherein said demethanolization is effected separate from said principal production unit, and said crude methyl chloride is recycled to said principal methyl chloride production unit, wherein said aqueous solution contains at least 15% by weight of hydrochloric acid and up to 100 g/l of methanol.

3. The process as defined by claim 2, said residual aqueous phase containing from 15 to 60 g/l of methanol.

4. The process as defined by claim 3, said residual aqueous phase containing at least 20% by weight of hydrochloric acid.

5. The process as defined by claim 2, said aqueous solution being maintained at a temperature of from 70° to 100° C. under a pressure of less than about 5 bars.

6. The process as defined by claim 2, wherein said demethanolization is carried out in a distillation column.

7. A process for the demethanolization of an aqueous solution comprising methanol and hydrochloric acid values, which comprises maintaining such solution, in the liquid phase and in the absence of a catalyst, at a temperature of from 50° to 150° C., under a pressure of less than about 8 bars and for a time sufficient to effect demethanolization, and recovering said methanol as crude methyl chloride;
    wherein said aqueous solution comprises a residual aqueous phase resulting from the reaction of methanol with hydrochloric acid in a principal methyl chloride production unit to produce methyl chloride, wherein said demethanolization is effected separate from said principal production unit and said crude methyl chloride is recycled to said principal methyl chloride production unit, and
    wherein said process is carried out in a distillation column comprising a reaction zone and a depletion zone, and wherein said aqueous solution is introduced essentially at the level of separation thereof.

* * * * *